United States Patent [19]

Pavlik

[11] 4,010,212
[45] Mar. 1, 1977

[54] PERFLUOROTERTIARYALKYL ETHERS

[75] Inventor: Frank J. Pavlik, West St. Paul, Minn.

[73] Assignee: Minnesota Mining and Manufacturing Company, St. Paul, Minn.

[22] Filed: June 14, 1976

[21] Appl. No.: 695,901

Related U.S. Application Data

[60] Division of Ser. No. 32,477, April 13, 1970, Pat. No. 3,981,928, which is a division of Ser. No. 538,556, March 30, 1966, abandoned, which is a continuation-in-part of Ser. No. 246,022, Dec. 20, 1962, abandoned, which is a continuation-in-part of Ser. No. 234,222, Oct. 30, 1962, Pat. No. 3,385,904.

[52] U.S. Cl. .............................................. 260/615 F
[51] Int. Cl.² ......................................... C07C 43/12
[58] Field of Search ................ 260/615 F, 615 BF

[56] References Cited

UNITED STATES PATENTS

| 2,713,593 | 7/1955 | Brice | 260/615 F |
| 2,754,318 | 7/1956 | Conly | 260/615 F |
| 3,385,904 | 1/1968 | Pavlik | 260/615 F |

Primary Examiner—Howard T. Mars

[57] ABSTRACT

A dihydroxyalkyl, perfluorotertiaryalkyl ether, said dihydroxyalkyl group having no more than 16 carbon atoms and said perfluorotertiaryalkyl group having the structure

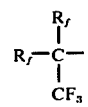

where $R_f$ is a perfluoroalkyl radical of less than 10 carbon atoms.

2 Claims, No Drawings

PERFLUOROTERTIARYALKYL ETHERS

This application is a division of Ser. No. 32,477, filed Apr. 13, 1970, now U.S. Pat. No. 3,981,928 which is a division of Ser. No. 538,556, filed Mar. 30, 1966, now abandoned, which is a continuation-in-part of my copending application, Ser. No. 246,022, filed Dec. 20, 1962, now abandoned, which application is a continuation-in-part of my prior and copending application, Ser. No. 234,222, filed Oct. 30, 1962, now U.S. Pat. No. 3,385,904.

This invention relates to a process for the treatment of fluorinated cyclic ethers having at least 4 carbon atoms to produce fluorinated tertiary alcohols and the production of derivatives of the alcohols so produced. In one aspect this invention relates to new and useful oxygenated derivatives produced from such fluorinated cyclic ethers and the corresponding tertiary alcohols.

Perfluorinated cyclic monoethers are known in the art. The perfluorinated cyclic monoethers are prepared as products and by-products from the electrochemical cell as disclosed in U.S. Pat. No. 2,519,983 - Simons, issued Aug. 22, 1950. Specific perfluorinated cyclic monoethers and the method of preparation thereof by the electrochemical cell are disclosed in U.S. Pat. No. 2,594,272 - Kauck et al, issued Apr. 29, 1952, and in U.S. Pat. No. 2,644,823 - Kauck et al, issued July 7, 1953.

The perfluorinated cyclic monoethers having at least 4 carbon atoms are useful as refrigerants, solvents, dielectric or insulating fluids, etc. They are noted for their chemical and physical stability and for their solvent action. These compounds are difficult to use as reactants or to convert to other chemical compounds, and few, if any, reactions with these compounds are known in the art. Since the perfluorocyclic monoethers having at least 4 carbon atoms are available in the art as a direct product and as a by-product, it is much to be desired to provide a method for the conversion of these cyclic monoethers to other chemical compounds which are useful.

It is an object of this invention to provide a process for the conversion of perfluorocyclic monoethers to other compounds.

It is another object of this invention to provide a new method for making perfluorinated tertiary alcohols.

Another object is to provide a method for the conversion of fluorinated tertiary alcohols to other useful compounds.

It is another object of this invention to provide new and useful condensation products of fluorinated tertiary alcohols, such as the esters and ethers.

Various other objects and advantages of the present invention will become apparent to those skilled in the art from the accompanying description and disclosure.

According to this invention, a perfluorocyclic monoether in which one of the vicinal carbon atoms is completely substituted with perfluoroalkyl radicals is decyclized in contact with hydrogen fluoride with or without the presence of a decyclization catalyst under conditions such that the cyclic ether chain is opened to produce the corresponding tertiary alcohol. The perfluorocyclic monoethers can be decyclized in the presence of catalysts, such as antimony pentafluoride, cesium fluoride, activated carbon and pyridine. The temperature conditions utilized are from about 20° C. to about 350° C. and pressures utilized are atmospheric or substantially elevated.

The perfluorocyclic monoethers as the starting compounds of this invention are designated perfluoroisoalkylene oxides-1,2 and the preferred ethers are represented by the following typical formula:

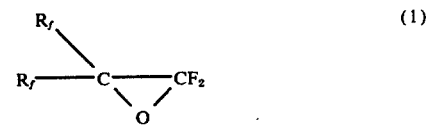

in which $R_f$ is defined as a perfluoroalkyl radical of less than 10 carbon atoms, preferably of 1 to 4 carbon atoms, and preferably at least one $R_f$ is a perfluoromethyl radical.

Examples of perfluorocyclic monoethers falling within the scope of the starting compounds of this invention include perfluoroisobutene-oxide-1,2; perfluoro-2-methylbutene oxide-1,2; and perfluoro-2-methylpentene oxide-1,2.

The amount of hydrogen fluoride is not critical except insofar as at least stoichiometric amounts in relation to the cyclic ether are required, but large excesses may be used without departing from the scope of this invention. The quantity of decyclization catalyst, if used, may vary over a considerable range. Usually the weight ratio of perfluorocyclic monoether to decyclization catalyst is between about 1:5 and 10:1.

The typical equation for the reaction involved for the perfluorocyclic monoethers is shown below:

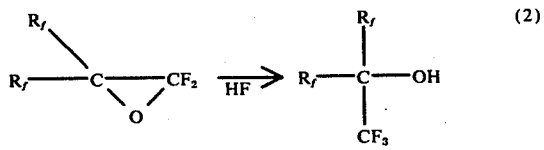

where $R_f$ is defined as above.

In accordance with one embodiment of this invention, the perfluoro-tertiary alcohols are converted to new and useful organic condensation products containing a perfluoro-tertiary-alkyl group in which the alkyl group contains at least one, preferably at least two, perfluoromethyl groups, and the perfluoro-tertiary-alkyl group has not more than 20, preferably 10, carbon atoms.

The new condensation products of this invention are obtained by reacting the above perfluoro-tertiary alcohol with an anionogenic organic compound of not more than 20 carbon atoms (an organic compound which is normally unionized but which is capable of generating a negative ion, anion, during the condensation reaction) by heating a mixture of the same, preferably in the presence of an organic solvent or liquid reflux medium. Particular examples of condensation products of the perfluoro-tertiary alcohol are the esters of organic acids (including anhydrides or acid halides) and ethers of aliphatic halides.

In the case of the esters, the organic acid moiety may be acyclic, alicyclic, aromatic or heterocyclic and may be saturated or may contain double bond unsaturation, such as ethylenic unsaturation. Preferably the organic acids contain at most halogen substitution, such as fluorine, chlorine or bromine. Examples of the acid moiety of the ester include carboxylic, sulfonic, phosponic, silicic, or cyanuric organic acids having not more than 18 carbon atoms. The esters of hydrocarbon caboxylic and hydrocarbon sulfonic acids are preferred.

In the case of the ethers, the aliphatic halide contains nonvinylic halogen such as fluorine, chlorine, bromine or iodine and may be acyclic or alicyclic, either saturated or ethylenically unsaturated. Preferably the aliphatic halide has at most halogen, hydroxyl or carboxy substitution. Examples of aliphatic halides include alkyl halide, alkylene halide, hydroxy alkyl halide and alkyl haloester having not more than 16 carbon atoms.

The perfluoro-tertiary alkyl condensation derivatives of this invention are particularly useful as surfactants and for applying to surfces, preferably in polymerized form, to render such surfaces, such as fabrics, oil and water repellent.

As previously mentioned, the perfluorocyclic monoether starting compounds can be prepared from the electrochemical cell. These ethers can also be prepared by oxidation of perfluoroolefins with hydrogen peroxide in an aqueous alkaline solution, such as in the presence of an aqueous alkali carbonate solution, e.g. sodium carbonate, at a temperature between about 0° C. and about 50° C.

The following Examples are offered as a better understanding of the present invention and relate to the conversion of the perfluorocyclic monoethers and their useful derivatives such as the perfluoro-tertiary alkyl and ethers (oxy alkylene esters), and the Examples are not to be construed as unnecessarily limiting the invention.

EXAMPLE I

To 10 ml. of acetone and 31 gs. of 30 % hydrogen peroxide at 0°–5° c., in a two-neck, one-liter glass flask with a magnetic stirrer and dry ice condenser was added 27 gs. (0.135 m.) of perfluoroisobutene. Water, 75 ml., containing 15 gs. $Na_2CO_3$ and 16 gs. $Na_2HPO_4$ was added dropwise during two hours. Stirring was continued for an additional twenty minutes. The product was distilled out through the dry ice condenser into a vacuum system. There was obtained 13.3 gs. of product, a 46% yield. Infrared spectroscopy indicated about 95% perfluoroisobutene oxide and no olefin.

EXAMPLE II

To 5 gs. of perfluoroisobutene oxide-1,2 in an Aminco 200-ml. bomb was charged 10 ml. of anhydrous liquid hydrogen fluoride. The bomb was placed in the Aminco rocker and heated and rocked at 250° C. for 64 hours. It was then cooled and the contents distilled through a tube containing sodium fluoride pellets to take up the unreacted hydrogen fluoride. The recovered fluorocarbon was condensed out in two fractions. The first fraction contained no unreacted perfluoroisobutene oxide and only a small amount of perfluoro-tertiary-butyl alcohol. The second or residue fraction contained a larger amount of perfluoro-tertiary-butyl alcohol as indicated by a definite infrared absorption at 2.7 microns.

EXAMPLE III

To 20 gs. of anhydrous hydrogen fluoride and 5 gs. of antimony pentafluoride in a 300-ml. stainless steel autoclave was charged 35 gs. of perfluoroisobutene oxide from Example I. The mixture was agitated in an Aminco rocking mechanism at 100° C. for sixteen hours. The product was then distilled out in vacuum through a steel tube containing sodium fluoride pellets to react wih the excess hydrogen fluoride. There was obtained 21 gs. of perfluoro-tertiary-butyl alcohol by distillation of the condensed fluorocarbon. It boiled at 48° C. and showed a hydroxy absorption in the infrared region at 2.7$\mu$. Nuclear magnetic resonance indicates the alcohol structure. The pKa of this material was determined to be about 5.5.

EXAMPLE IV

Sodium perfluoro-tertiary-butylate, 4.76 gs., was prepared from sodium meal and perfluoro-tertiary-butyl alcohol of Example III in anhydrous ethyl ether at 5° C. initially, then gradually warming to 25° C. The ether, after filtration of the solution from insoluble salts, was removed in vacuum at 1 mm. and 40° C. To this salt was added 50 ml. petroleum ether (dried over $P_2O_5$), a trace of pyrogallic acid and 1.7 gs. acrylyl chloride. The reaction was stirred at room temperature for 64 hours. The mixture was filtered, washed with aqueous sodium bicarbonate and water and finally dried over Drierite and sodium sulfate. Distillation through a 10-plate column gave 2.3 gs. of product boiling at 99°–101° C. A yield of 43% was obtained. Gas liquid chromatography indicated a purity of 98%. Infrared spectroscopy indicated perfluoro-tertiary-butyl acrylate by absorptions at 5.5$\mu$, 6.1$\mu$ and 7.8$\mu$. This material when polymerized and applied on textiles gave oil and water repellency to the textile.

EXAMPLE V

Perfluoro-tertiary-butyl methacrylate was prepared from perfluoro-tertiary-butyl alcohol and methacrylyl chloride with 2-methyl pyridine as the acid acceptor without added solvent. The yield was 78%. The boiling point was 30° C./0.5 mm. This material is useful as a monomer for making plastics and resins.

EXAMPLE VI

Sodium perfluoro-tertiary-butylate, 15.3 gs. (0.059 m.), prepared in a manner similar to Example IV, and 0.08 m. ethylene bromohydrin were heated at reflux in methylethyl ketone for 88 hours. An 85% yield of 2-(perfluoro-tertiary-butoxy) ethanol $(CF_3)_3COCH_2CH_2OH$ boiling at 125° C./740 mm. was obtained by distillation. Ethylene oxide and the perfluoro-tertiary-butyl alcohol or the sodium salt thereof gave the same product as above, but also higher boiling liquids. This material is useful for conversion to acids and esters and directly as a solvent and a plasticizer.

Preparation of the methacrylate of the above 2-(perfluoro-tertiary-butoxy) ethanol was accomplished as follows: To 9 gs. (0.032 m.) of tert-$C_4F_9OCH_2CH_2OH$ were added to 5 gs. (0.048 m.) of $CH_2=C(CH_3)COCl$, 20 ml. of ethyl ether and 0.05 m. of pyridine and the mixture was stirred overnight at room temperature. Distillation gave 7.2 gs. of perfluoro-tertiary-butoxy ethyl methacrylate, boiling at 35° C./1 mm. Analysis by infrared spectroscopy indicated an unsaturated ester. Polymerization of this monomer afforded a polymer which showed water and oil repellency for application to textiles and leather as a protective coating.

The following derivatives are also made by reaction of the above 2-(perfluoro-tertiary-butoxy) ethanol with diisocyanates, diacids, silanes and the like;

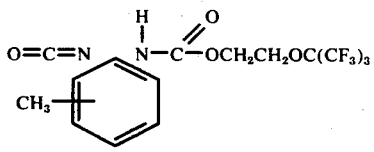

perfluoro-tertiary-butoxy-ethyl (isocyanotoluene) carbamate

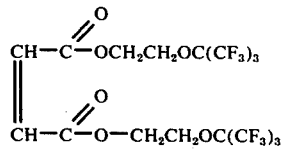

di-perfluoro-tertiary-butoxy ethyl maleate

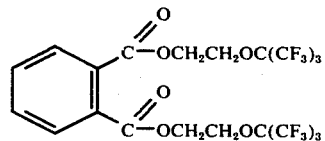

di-perfluoro-tertiary-butoxy ethyl phthalate

[(CF$_3$)$_3$COCH$_2$CH$_2$O]$_2$SiCl$_2$  6 ps dichloro,di(perfluoro-tertiary-butoxy ethyloxy)silane

EXAMPLE VII

In a sealed ampoule 1.5 gs. of a p-bromobenzene-sulfonyl chloride and 1.5 gs. of sodium perfluoro-tertiary-butylate as made in Example IV were heated at 155° C. for sixteen hours. The ampoule was cooled and opened into a vacuum manifold system. Extraction of the solid with petroleum ether left 0.5 g. of insoluble solid. The petroleum ether-soluble material yielded an oil which slowly crystallized and melted at 32°–35° C. Infrared spectroscopic analysis indicated this oil to be perfluoro-tertiary-butyl p-bromobenzene sulfonate. Elemental analysis was as follows:

|   | Calculated | Found |
|---|---|---|
| C | 25.7 | 27.0 |
| S | 6.8 | 7.3 |
| F | 36.4 | 34.2 |

Perfluoroalkyl arylsulfonates are useful for making many organic chemicals containing the perfluoroalkyl group, such as ethers, halides, alkylbenzenes, etc.

Perfluoro-tertiary-butyl chlorosulfonate has also been synthesized in the above manner using sulfuryl dichloride and has similar utility.

EXAMPLE VIII

From 12.45 gs. (0.075 m.) of ethyl bromoacetate and 19.35 gs. (0.075 m.) of NaOC(CF$_3$)$_3$ in 15 ml. of methylethyl ketone stirred and heated at reflux 73 hours there was obtained 13 gs. (50%) of ethyl(perfluoro-tertiary-butoxy) acetate boiling at 140°–145° C./750 mm. Hydrolysis of this ester in 12% aqueous sodium hydroxide overnight at room temperature gave after acidification and extraction (perfluoro-tertiary-butoxy) acetic acid which crystallized from ether-hexane and melted at 85°–87° C.

A chrome complex was made from this acid, and paper and leather were treated with its solution in isopropyl alcohol. The results indicated good water and oil repellency properties of the treated paper and leather. Other derivatives of this acid can be made which are useful in paints, plastics, elastomers, i.e. vinyl esters as monomers and diol esters as plasticizers.

EXAMPLE IX

To 10 ml. of methyl ethyl ketone were added 5.16 gs. (0.02 m.) NaOC(CF$_3$)$_3$ and 4.66 gs. (0.02 m.) 11-bromoundecene. To promote the reaction, 0.35 g. NaI was added and the reaction heated for 192 hours at reflux. Filtration yielded a total of 1.15 g. of a mixture of NaBr and NaI or 56% conversion based on NaBr content. Distillation of the filtrate through a threeplate column gage 3.18 gs. of 11-(perfluoro-tertiary-butoxy) undecene boiling at 56° C./0.5 mm., d. 1.22, n$_D^{26}$ 1.3678. Infrared spectroscopy indicated the characteristic absorptions for unsaturation and fluorocarbon.

Derivatives of this material can be made as follows:

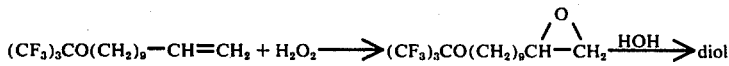

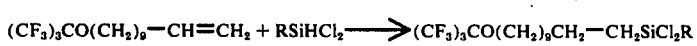

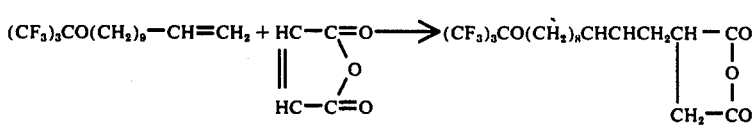

Other similar ω-bromoundecyl derivatives can be made, such as alcohols and acids. These derivatives are useful as plasticizers and monomers for making polymers.

EXAMLE X

To 0.87 g. (0.05 m) of 2,4-toluene-diisocyanate in 5.2 gs. of ethyl acetate was added a trace of phenyl mercuric acetate and 2.36 gs. (0.01 m.) perfluoro-tertiary-butyl alcohol. The ampoule was sealed and heated at 100° C. and agitated for seventeen hours. An infrared spectrum of the recovered solution showed the diurethane di-perfluoro-tertiary-butyl-toluene dicarbamate, was present in the product and useful for making urethane type resins.

EXAMPLE XI

To 13.0 gs. (0.05 m.) NaOC(CF$_3$)$_3$ was added 25 ml. dry petroleum ether (boiling at 30°–60° C.). This was cooled to −80° C., and 16.4 gs. of C$_2$H$_5$SiCl$_3$ (0.1 m.) was added and stirred overnight at −80° C. The reaction mixture was warmed to 50° C. and stirred 20 hours. After cooling, the mixture was filtered and the filtrate distilled through a three-plate column. There was obtained 6.0 s. of a fraction, boiling at 97°–99° C., containing some EtSiCl$_3$ and 3.5 gs. of dichloroethyl-perfluoro-tertiary-butoxy silane which boiled at >99° C. Infrared analysis of the latter indicates the above material. This product can be hydrolyzed with water to produce a silicone useful for coating textile fabrics.

EXAMPLE XII

NaOC (CF$_3$)$_3$, 6.45 gs., (0.025 m.) in acetone, was added to 5 gs. (0.055 .) cyanuric chloride in acetone at 0° C. during 105 minutes. Overnight stirring, 22 hours, was conducted at room temperature. The reaction mixture was then filtered and the acetone removed from the filtrate in vacuum. There was recovered 2.5 gs. of light yellow liquid and unreacted cyanuric chloride. Infrared indicated desired perfluoro-tertiary-butyl dichlorocyanurate. This is useful for reaction with amines and subsequently with formaldehyde to produce textile treating resins.

EXAMPLE XIII

From 3.87 gs. (0.03 m.) (CH$_3$)$_2$SiCl$_2$ and 15.4 gs. (0.06 m.) NaOC(CF$_3$)$_3$ in 35 ml. petroleum ether 30°–60° C., there was obtained after 68 hours at reflux 6.0 gs. of distilled (10-plate column) product, boiling at 146° C. Infrared analysis indicated no OH or carbonyl absorptions. Thus the product was (CH$_3$)$_2$Si(OC$_4$F$_9$)$_2$ useful as a solvent.

EXAMPLE XIV

To 2.2 gs. triethyl amine and 3.72 gs. perfluoro-tertiary-butyl alcohol in 10 ml. dichloromethane at 0°–5° C. was added drop-wise and with stirring 5.64 gs. perfluoro-methane sulfonic anhydride. Stirring at room temperature was continued 88 hours. The volatile material was then distilled from the nonvolatile in vacuum, then redistilled. There was obtained 3.6 gs. at a boiling point of 91° C. Analysis by infrared and NMR spectroscopy indicated the desired material, perfluoro-tertiary-butyl perfluoromethanesulfonate, which is useful as a plasticizer for fluorocarbon resins.

EXAMPLE XV 8.6 gs. (0.033 m.) NaOC(CF$_3$)$_3$, 4.0 gs. ClCH$_2$CHOHCH$_2$OH and 4.0 gs. ethylene glycol and 9 ml. methylethyl ketone were heated at reflux 67 hours. 1.64 gs. of salts were filtered off; theory 1.93 gs. The product was phased out by adding water and washed three times with water. There were recovered 9.0 gs. of product which was dried over Drierite. Distillation through a 4-plate column at 1 mm. gave 4.06 gs. of a fraction boiling at 60°–65° C., n$_D$$^{23}$ C. 1.3492. Infrared indicated C$_4$F$_9$OCH$_2$CHOHCH$_2$OH, useful for preparation of polyurethanes and polyesters.

EXAMPLE XVI

To 2.1 gs. (0.02 m.) of 2-methylpyridine, cooled to 0°–5° C., was added dropwise with stirring 4.2 g. of trifluoroacetic anhydride. Then 4.72 g. of perfluoro-tertiary-butyl alcohol was added to the above mixture. Stirring was continued at room temperature for 48 hours. Distillation of the reaction mixture gave perfluoro-tertiary-butyl perfluoroacetate boiling at 57°–58° C. at 740 mm. Infrared spectroscopy of the sample showed ester absorption at 5.4μ. This compound is useful as a low boiling inert heat exchange liquid.

EXAMPLE XVII

This perfluoro-tertiary-butoxy acid was prepared by dissolving 2.6 gs. (0.01 m.) of (CF$_3$)$_3$CONa and 4.1 gs. (0.014 m.) Br(CH$_2$)$_{10}$CO$_2$C$_2$H$_5$ in 15 ml. of methyl ethyl ketone and heating the solution at reflux, about 80° C., for 100 hours.

The solvent was stripped under vacuum and replaced by 50 ml. of concentrated isopropyl alcohol containing 2 gs. of dissolved KOH. The solution was refluxed for 2 hours. The isopropyl alcohol was then evaporated under vacuum and 10 ml. of concentrated aqueous HCl added to neutralize the base and liberate the acid. The aqueous solution was then extracted with 50 ml. of isopropyl ether, in several portions, and the ether extract evaporated. An aqueous solution of the sodium salt of the acid was prepared by dissolving 0.3 gram of the residue in 30 ml. of water and neutralizing with dilute aqueous sodium hydroxide to the phenolphthalein end point. The resulting 1% solution showed a surface tension at 24° C. of 20 dynes per sq. cm. This surface tension is about the same as is shown by a 1% solution of sodium perfluoro butyrate, which contains approximately twice the fluorine content as the present acid. This compound is very good as a surfactant or to treat textiles or leather for oil and water repellency when converted to the chrome complex.

EXAMPLE XVIII (CF$_3$)$_3$CO(CH$_2$CH$_2$O)$_n$H was prepared in a sealed glass ampoule from the reaction of 3.5 grams (0.076 mole) of ethylene oxide with 1 gram (0.0035 mole) (CF$_3$)$_3$COCH$_2$CH$_2$OH and 50 mg. KOH at 100° C. and autogeneous pressure for 16 hours. From the ratio of reactants, the average value of n in the polyether alcohol would be about 20. A 1% aqueous solution showed a surface tension of 28 dynes per sq. cm. at 25° C. The starting alcohol, (CF$_3$)$_3$COCH$_2$CH$_2$OH, in a 1% aqueous solution showed a surface tension of 41 dynes. This compound is useful as a surfactant or can be converted to the acrylate and polymerized and then used to treat fabrics for oil and water repellency.

Various alterations and modifications of reaction conditions may become apparent to those skilled in the art without departing from the scope of this invention.

Having described my invention, I claim:

1. 3(perfluoro-tertiary-butoxy)dihydroxy propanol-1,2.

2. A dihydroxyalkyl, perfluorotertiaryalkyl ether, said dihydroxyalkyl group having no more than 16 carbon atoms and said perfluorotertiaryalkyl group having the structure

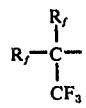

where R$_f$ is a perfluoroalkyl radical of less than 10 carbon atoms.

UNITED STATES PATENT AND TRADEMARK OFFICE
CERTIFICATE OF CORRECTION

PATENT NO. : 4,010,212
DATED : March 1, 1977
INVENTOR(S) : FRANK J. PAVLIK

Page 1 of 2

It is certified that error appears in the above-identified patent and that said Letters Patent are hereby corrected as shown below:

In Column 3, line 4, the first word, "caboxylic", should read -
-- carboxylic --.

In Column 3, lines 30 and 31, between the words "alkyl" and "and", a word has been omitted and should read -
-- alkyl esters and --.

In Column 4, line 15, after the word "sodium", the word "meal" should read -
-- metal --.

In Column 4, line 57, between the words "added" and "5 gs." the word "to" should be deleted to read -
-- added 5 gs. --.

In Column 6, line 35, second word "gage" should read -
-- gave --.

In Column 6, line 36, "undecene boiling at 56°C./0.5 mm., d. 1.22, $n_D^{26}$ C." should read -
-- undecene boiling at 56°C./0.5 mm., d. 1.22, $n_D^{26°C.}$ --.

UNITED STATES PATENT AND TRADEMARK OFFICE
CERTIFICATE OF CORRECTION

PATENT NO. : 4,010,212
DATED : March 1, 1977
INVENTOR(S) : FRANK J. PAVLIK

Page 2 of 2

It is certified that error appears in the above-identified patent and that said Letters Patent are hereby corrected as shown below:

In Column 7, line 10, after the word "obtained", "6.0 s." should read -
-- 6.0 gs. --.

In Column 7, line 18, after 5 gs. "(0.055 .)" should read -
-- (0.055 m.) --.

In Column 7, line 40, "3.72 gs." should read -
-- 4.72 gs. --.

In Column 7, line 62, "of a fraction boiling at 60° - 65°C., $n_D^{23}$ C." should read -
-- of a fraction boiling at 60° - 65°C., $n_D^{23°C.}$ --.

Signed and Sealed this

Seventeenth Day of May 1977

[SEAL]

Attest:

RUTH C. MASON
*Attesting Officer*

C. MARSHALL DANN
*Commissioner of Patents and Trademarks*